United States Patent
Hoagland

Patent Number: 5,249,961
Date of Patent: Oct. 5, 1993

[54] PORTABLE PET TEETH-CLEANING ABRASIVE INSTRUMENT

[76] Inventor: Richard W. Hoagland, Lake Trail East, Morristown, N.J. 07960

[21] Appl. No.: 989,692

[22] Filed: Dec. 14, 1992

Related U.S. Application Data

[63] Continuation-in-part of Ser. No. 951,887, Sep. 28, 1992.

[51] Int. Cl.$^5$ .............. A61D 5/00; A46B 9/04; A47K 7/02; A47L 13/46
[52] U.S. Cl. .................. 433/1; 15/167.1; 15/244.1
[58] Field of Search .......... 433/1; 15/167.1, 167.2, 15/210.1, 244.1

[56] References Cited

U.S. PATENT DOCUMENTS

| | | | |
|---|---|---|---|
| 1,635,924 | 7/1927 | Buckley | 15/210.1 |
| 3,337,893 | 8/1967 | Fine et al. | 15/167.1 X |
| 3,491,396 | 1/1970 | Eannarino et al. | 15/167.1 X |
| 3,577,582 | 5/1971 | Aston | 15/244.1 |
| 3,613,143 | 10/1971 | Muhler et al. | 15/167.1 |
| 4,155,139 | 5/1979 | Corcoran | 15/244.1 |
| 4,628,564 | 12/1986 | Yousset | 15/244.1 X |

Primary Examiner—Gene Mancene
Assistant Examiner—Nicholas D. Lucchesi
Attorney, Agent, or Firm—William T. Hough

[57] ABSTRACT

A portable instrument having a handle with a distal end with a flattened face having mounted thereon an elongated flexible pad having an abrasion-resistent upper face and having a mid-portion and opposite end portions, with the opposite end portions turned-under the mid-portion and with the turned-under portions mounted on the flattened face, the turned-under portions resulting in leaving exposed the upper remaining exposed upper mid-portion and convoluted convex opposite outer side faces or surfaces, the exposed mid-portion and convoluted convex opposite side faces embodying abrasive composition mounted thereon including microscopic abrasive mineral particles embedded in phenolic resin and/or abrasive(s) embedded in or adhered to nylon fibrous strands.

19 Claims, 3 Drawing Sheets

PORTABLE PET TEETH-CLEANING ABRASIVE INSTRUMENT

This invention is a continuation-in-part of the co-pending parent U.S. patent application U.S. Ser. No. 07/951,887 filed Sep. 28, 1992. The present invention constitutes an improvment on that parent application invention, relating to a device or instrument for the abrasive cleaning of teeth of a pet. The entire disclosure of the above-described parent U.S. patent application Ser. No. 07/951,887 is hereby and herewith incorporated by reference into and as a part of this continuation-in-part patent application, in support of the present improvements set-forth herein.

PRIOR ART

While no relevant prior art was located in a patentability novelty search, patents of interest located are as follow, in a search in United States Patent & Trademark Office United States Class 15, subclass 167.1. None of the patents located related directly to use in the cleaning of teeth of pets, such as dogs or cats. U.S. Pat. No. 4,528,564 granted Dec. 16, 1986 to Youssef is directed to a device for directing liquid through bristles of a pointed end-mounted sponge having associated bristles, designated as being a toothbrush structure. U.S. Pat. No. 4,576,190 granted Mar. 18, 1986 to Yousseff likewise is directed to a non-abrasive sponge-mounted tooth-cleaning device. U.S. Pat. No. 5,044,041 to Ljungberg granted Sep. 3, 1991 is directed to a toothpick type device having oppositely spaced apart rows of serially-arranged consecutive teeth of thermoplastic. All other patents are directed to variations on toothbrushes, such as U.S. Pat. No. 3,337,893 granted on Aug. 29, 1967 to Fine et al. having opposite a bristles-side, an opposite face thereof carrying resilient sponge with woven fibers having twisted sharp cutting edges, and U.S. Pat. No. 323,305 issued Jul. 28, 1885 to Evans to a device called a toothbrush having surface of paraffin-soaked woven and rolled fabric, and U.S. Pat. No. 1,801,915 granted Apr. 21, 1931 to Gray directed to a handle mounting-structure for the mounting of a block of rubber thereon, and U.S. Pat. No. 1,599,191 granted Jun. 3, 1952 to Meunier directed to looped bristles, and U.S. Pat. No. 2,877,483 granted Mar. 17, 1959 directed to a mounted rubber sponge encased by plastic woven threads having interstices (holes) therebetween, and U.S. Pat. No. 1,470,710 granted Oct. 16, 1923 to Davis to a toothbrush having a plurality of abrasive penetrative straight stiff filaments within and enveloped by yielding fibrous vegetable or other cellulose, such that the filaments may be pushed through space to contact teeth during brushing. While no patent is known thereto, also there is a commercial finger-mountable tab of gauze (no apparent abrasive composition thereon) for use to clean a pet's teeth, having no disclosure as to its content and no mounting handle structure that would permits viewing and that would remove the risk of being bitten by the pet. The present inventor has herefore made concerted but unsuccessful attempts to clean the teeth of a pet by use of a conventional nylon bristles toothbrush, including use therewith of dental dip and also with dentifrice. Each of Linzey U.S. Pat. No. 5,027,796 and Picard U.S. Pat. No. 1,219,147 and Goldstein et al. U.S. Pat. No. 2,736,917 illustrated shaped molded composition shaped to have curved surfaces. None of these are layered pad structure turned-under itself and none thereof are dealing with a pad having a tougher (less apt to wear away during use) surface than the side-faces thereof, a problem faced and overcome by the present invention; also, of major importance, none of these foregoing patents nor the Evans U.S. Pat. No. 323,305 form a convoluted convex portions (resulting from the turning-under of the unwoven pad of the present invention having its convex surface extending far beyond to overhang significantly beyond side face(s) of the brush head—such that none of these nor other patents are directed to nor achieve the benefits of the present invention.

BACKGROUND TO THE INVENTION

Typically commercially available toothbrushes have elongated handles with monofilament bristles mounted on a flattened laterally-facing face of a flattened toothbrush head at the distal end of the handle. The thin flexible typically nylon bristles are smooth monofilaments of which the ends of the bristles are cut-off at right angles to form the flat brush area. Cleansing of a person's teeth is accomplished by action of the sides and ends of the nylon bristles which move over the teeth. The person holding the handle of the toothbrush manipulates the angle and direction of the brush so as to access most of the tooth surface. A dentifrice, such as toothpaste is used for its foaming action so that loosened food particles can be more readily removed.

The above-described conventional toothbrush and the above-described mechanism thereof in attempted tooth cleaning, does not effectively remove stains and/or plaque. The bristles are ineffective in removing stains and/or semi-hardened plaque. With the present technology typically described above, a person must await a scheduled visit to the dentist or dental hygienist in order to have the plaque and stains removed by the use of metal scraping tools and/or electric cleaning device(s) in combination with typically a gritty paste.

A prior device (instrument) for attempted cleaning of the teeth of a dog, is the standard or conventional toothbrush, sometimes used in combination with special enzymatic dentifrice. As in cleaning human teeth with a toothbrush, this above-described approach with dogs, fails to remove established plaque and/or tartar from the dog's teeth, and prolonged and/or over zealous attempts to get at and attempts to remove the plaque and/or tartar from the dog's teeth, can cause pain and/or eventual exhaustion of patience of the dog or other pet, and/or irritability of the pet, perhaps associated with snapping and/or biting. Present approaches at cleaning a pet's teeth moreover is extremely slow and tedious and fails to do an effective or satisfactory job in removal of yellow stains that are so common on a dog's teeth, for example. Use of metal dental instruments in attempts to clean (for example) a dog's teeth, requires great care to avoid hurting or causing pain or injury to the tender tissue, or to cutting or tearing such tissue, even with the exercise of great care and patience. Moreover, the task is made more difficult normally arising from long or protracted periods between attempts to clean the teeth of a pet, allowing the teeth of the dog or cat, (for example) to accumulate yellow and brownish plaque and tartar, and for it to be hardened to a greater degree than typically on human teeth that receive a higher degree and more frequent care.

OBJECTS OF THE INVENTION

While the tooth cleaning device(s) of inventor's parent application above-noted, works very well in the cleaning of pet's teeth, inventor found that the exposed edges of the pad of fibers wore-away much faster than desired and much faster than the hardened upper surface of the previously described commercially available pad. The wearing of the side more frayable portions accordingly substantially and rapidly dimenished the longivity of effective use of the pad of Applicant's inventive device as a whole.

Also with the prior art tooth cleaning devices, as well as with the tooth cleaning devices of the parent application, substantially straight upwardly and downwardly extending sides of the fibrous pad as heretofore mounted on the flattened upper and/or lower face(s) of the distal end of the elongated handle structure, proved substantially ineffective and/or difficult to maneuver in a manner that would facilitate reaching especially areas between the teeth and/or to make use—as situations might demand and/or be desirable—of the entire exposed surface of the mounted fibrous pad.

Additionally, the linear or substantially flat and/or non-yielding upper top surface and/or the upwardly-extending opposite side surfaces of prior art cleaning devices and of the fibrous pad of the parent patent application, failed to make best use of fibrous surfaces to reach between-teeth areas, as well as preventing yielding of certain portions while adjacent areas might move forward to better reach and clean away otherwise substantially inaccessible area(s) that heretofore might require a pick of some sort.

Accordingly, objects of the invention include the overcoming and/or avoiding of problems and difficulties above-described.

Another object is to obtain a novel portable device (instrument) utilizable to effectively and safely clean teeth of a pet devoid of hurting or injuring the pet, and/or devoid of irritating gum tissue of the pet, and/or devoid of hazardous risk of being bitten by the pet during a tooth-cleaning operation.

Another object is to obtain improved accessability to heretofore substantially inacessable areas at, around and/or between teeth, to more effectively and comprehensively clean away and/or scale-away debris during the cleaning of a pets teeth utilizing the device(s) of the present invention.

Another object is to improve the shape of the mounted pad in a manner and to an extent to effectively facilitate improved keeping abrasive surfaces away from delicate tissue above and/or below the gums of the pet while the device is being rubbed for example horizontally across the teeth.

Another object is to obtain a yielding but resilient pad-surface(s) characteristics for the top and/or side surfaces for improved cleaning together with reduced possibility of injuring tissue and/or inflicting pain to the pet, during the cleaning of and/or scaling away of debris from tooth surfaces of the pet.

Another object is to improve acceptability of exposed pad surface(s) and improved partial retainability of those surfaces, of dentifrice and/or other cleaning and/or lathering composition(s) to make such automatically available during and more-likely throughout a cleaning and/or de-scaling procedure in the cleaning of a pet's teeth.

Another object is to improve the final operational shape of the mounted fibrous pad such that during a cleaning and/or descaling operation in the cleaning of a pet's teeth, there is improved accessability to area(s) close to the gum(s) in efforts to remove, for example, plaque and/or tartar.

Another object is to obtain a finally mounted fibrous pad having one or more advantages, together with the characteristic of retaining and/or returning to initial shape during and after prolonged and/or repeated cleaning operations in the cleaning of the teeth of a pet.

Another object is to have the fibrous pad mounted such that less hard and/or frayable and/or less durable surfaces of the fibrous structure are positioned to avoid wearing-contact with teeth or other surfaces during a cleaning of a pet's teeth, so as to prolong the effective life and effectiveness of the present inventive cleaning device.

Other objects become apparent from the preceding and following disclosure.

SUMMARY OF THE INVENTION

The invention may be broadly defined as a portable handle-mounted pet teeth-cleaning device. The device, as a combination, includes the follwing essential elements:

(a) A teeth surface-cleaning structure(s) and mechanism(s) thereof is/are provided and is/are effective for and in the rubbing against teeth surfaces to abrasively clean and/or abrasively scale-away debris from surfaces of teeth of a pet. The teeth surface-cleaning structure(s) and mechanism(s) thereof includes one or more teeth-cleaning fibrous pad structure(s).

(b) A handle structure(s) and mechanism(s) thereof is provided that effectively mounts thereon the teeth surface-cleaning structure(s) and mechanism(s) thereof. The handle structure provided effectively makes possible the grasping thereof with fingers of a person while cleaning a pet's teeth and enabling maneuvering the teeth surface-cleaning structure(s) and mechanism(s) thereof against a pet's teeth during cleaning of debris from a pet's teeth.

The handle structure(s) and mechanism(s) thereof has/have an elongated distal end with a substantially flattened face(s) adapted to mount permanently the teeth-cleaning pad structure(s) and mechanism(s) thereof thereagainst.

(c) There is/are provided pad mounting structure(s) and mechanism(s) thereof that effectively secure the teeth-cleaning pad structure onto the substantially flattened face.

The teeth-cleaning pad structure(s) include(s) a substantially flexible flattened elongated pad(s) having opposite first and second end-portions and an intermediate portion therebetween.

The flexible flattened elongated pad(s) (one or more thereof) has/have opposite first and second faces extending between the opposite first and second opposite end-portions.

There is/are a thickness(es) between the first and second opposite faces forming opposite side third and fourth faces; there is/are respectively one thereof at each of the first and second opposite end-portions.

Each of the opposite side third and fourth faces has/have substantially the above-stated thickness(es).

The opposite first face(s) has/have a substantially durably hardened exterior face(s) that is/are substantially resistant to significant abrasion when rubbing against a pet's tooth surfaces to remove debris from the tooth surfaces of a pet.

At-least one of the end portions is/are downwardly bent sufficiently to form at-least one convoluted convex outer side face and at-least one turned-under portion positioned at-least partially beneath the intermediate portion.

Each of the at-least one turned-under portions has/have a lower-most face(s).

Each lower-most face(s) is/are permanently mounted by the pad mounting structure(s) and mechanism(s) thereof onto the substantially flattened face(s) of the elongated distal end.

The elongated distal end above-described, has a circumscribing side face substantially circumscribing the above-described substantially flattened face. The circumscribing side face includes a distal end face and opposite lateral faces of the distal end portion (normally referred to as the head). The convoluted portion and/or its outer convex surface(s) extends a significant distance beyond and thus overhangs the side face at one or more of the distal end face and/or opposite lateral face(s). The overhang is sufficiently beyond the side face (a predetermined distance) sufficiently that the convoluted convex outer side face(s) may be abrasively rubbed against tooth surfaces devoid of contacting gum and/or tooth surfaces with the circumscribing side face of the head (distal end) of the mounting handle structure.

In a first preferred embodiment as an improvement on the broad above-defined inventive embodiment(s), the flattened face(s) extends substantially longitudially along a longitudinal axis of the elongated distal end.

In this first preferred embodiment, each of the elongated distal end portion(s) extends substantially transversely to the longitudinal axis of the elongated distal end. Each of the distal end portions has/have the convoluted convex outer side face(s) as opposite first and second convoluted convex outer side faces.

Each of the distal end portions has/have the turned-under portion as first and second turned-under portions substantially in juxtaposition to one-another.

In a second preferred embodiment, as an improvement on the broad generic embodiment as initially above-described, the opposite side faces each consists essentially of abrasive composition sufficiently abrasive to abrade-away residual coating debris from tooth surfaces of a pet's teeth when rubbed thereagainst.

In a third preferred embodiment, as an improvement on the second preferred embodiment, the first opposite face consists essentially of abrasive composition sufficiently abrasive to abrade-away residual coating debris from tooth surfaces of a pet's teeth when rubbed thereagainst.

In a fourth preferred embodiment as an improvement on the third preferred embodiment, the abrasive composition comprises at-least predominantly nontoxic resinous composition.

In a fifth preferred embodiment as an improvement on the fourth preferred embodiment, the abrasive composition consists essentially of a plurality of strands of synthetic fiber coated by the non-toxic resinous composition.

In a sixth preferred embodiment as an improvement on the fifth preferred embodiment, the resinous composition consists essentially of predominantly at-least one of a phenolic resin and an acrylic resin.

An a seventh preferred embodiment as an improvement on the sixth preferred embodiment, the first abrasive structure includes first mineral particles supported by the resinous composition on at-least the plurality of synthetic fibrous strands.

In an eighth preferred embodiment as an improvement on the seventh preferred embodiment, the mineral particles are microscopic in size.

In a ninth preferred embodiment as an improvement on the eighth preferred embodiment, the synthetic fibrous strands includes predominantly at-least one of nylon strands and polyester strands.

In a tenth preferred embodiment as an improvement on the first preferred embodiment, the improvement thereto is the same as the second preferred embodiment improvement.

In an eleventh preferred embodiment as an improvement on the first preferred embodiment, the improvement thereto is the same as the third preferred embodiment improvement.

In a twelfth preferred embodiment as an improvement on the eleventh preferred embodiment, the improvement thereto is the same as the fourth preferred embodiment improvement.

In a thirteenth preferred embodiment as an improvement on the eleventh preferred embodiment, the improvement thereto is the same as the fifth preferred embodiment.

In a fourteenth preferred embodiment as an improvement on the twelfth preferred embodiment, the improvement thereto is the same as the sixth preferred embodiment.

In a fifteenth preferred embodiment as an improvement on the twelfth preferred embodiment, the improvement thereto is the same as the seventh preferred embodiment.

In a sixteenth preferred embodiment as an improvement on the fifteenth preferred embodiment, the improvement thereto is the same as the eighth preferred embodiment.

In a seventeenth preferred embodiment as an improvement on the sixteenth preferred embodiment, the improvement thereto is the same as the ninth preferred embodiment.

In an eighteenth preferred embodiment as an improvement on the generic broad invention above-described, the elongated distal end has a terminal distal portion. The flattened face extends substantially longitudinally along a longitudinal axis of the elongated distal end to the terminal portion thereif. Each of the elongated distal end portions extends substantially longitudinally along the longitudinal axis of the elongated distal end. At least one of the distal end portions is turned-under one of the first and second end-portions corresponding thereto, at the terminal distal end.

The invention may be better understood by making reference to the following figures.

THE FIGURES

FIGS. 1 through 3 diagrammatically and symbolically represent a common embodiment, in so far as the element(s) illustrated therein.

FIGS. 4 through 6 diagrammatically and symbolically represent a different common embodiment, in so far as the element(s) illustrated therein.

FIGS. 7 through 9 diagrammatically and symbolically represent another different common embodiment, in so far as the elements illustrated therein.

FIG. 10 diagrammatically and symbolically illustrates an alternate pad that would embody the features of each and both of the pads of FIGS. 3 and 6.

FIG. 1 illustrates a side view of a typical device of the present invention, noting that the hand-grasping portion of the handle could be of any desired alternate design or shape, the straight elongated finger-holding hand or finger-grasping portion thereof being merely typically illustrated herein. More importantly, in this side view, there is seen an elevation plan view of one side of the mounted abrasive fibrous pad of the present invention, noting that the other side would have substantially the same and/or identical appearance. The illustrated side is curved in the above-described convoluted convex outer side face or surface, not readily discernible in this view.

FIG. 2 illustrate the embodiment of FIG. 1, as taken in cross-sectional view along line 12-2 of FIG. 1.

FIG. 3 illustrated the same fibrous pad of FIGS. 1 and 2, but in greater detail, in an elevation plan view thereof prior to its folding.

Figure 1:
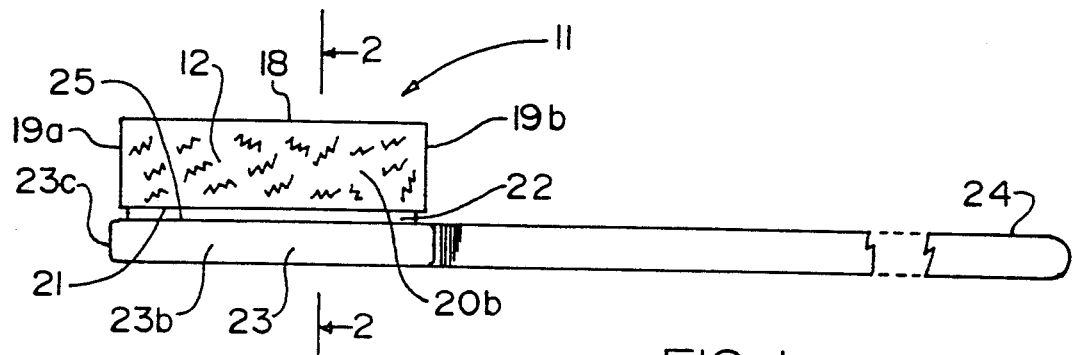
Figure 2:
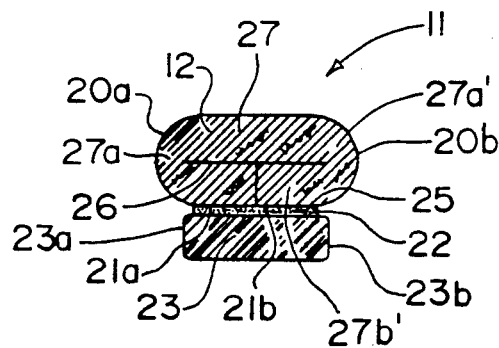
Figure 3:
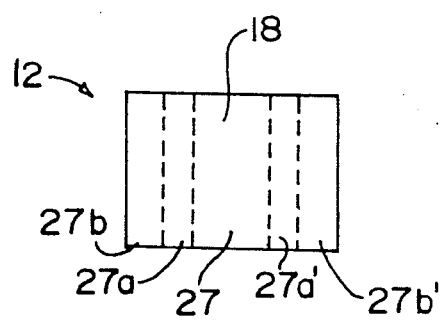
Figure 4:
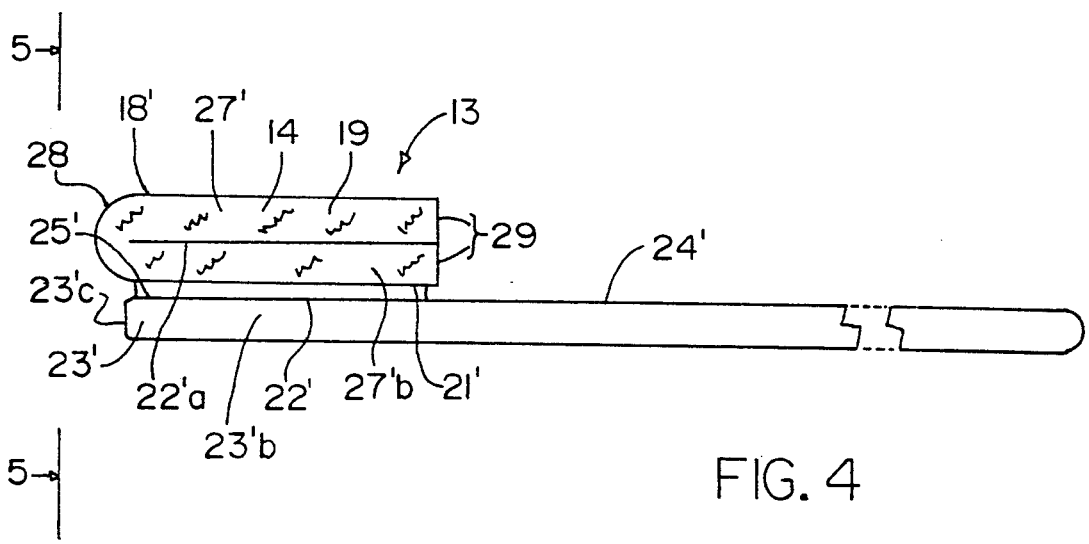
FIG. 4 illustrates an elevation plan side view of an alternate other embodiment of the invention shown in an in-part view of the handle portion.
Figure 5:
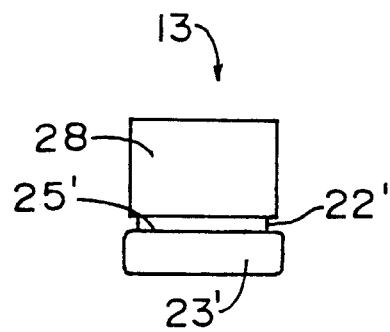
FIG. 5 illustrates an end elevation plan view of the embodiment of FIG. 4, as taken along lines 5—5 of FIG. 4.
Figure 10:
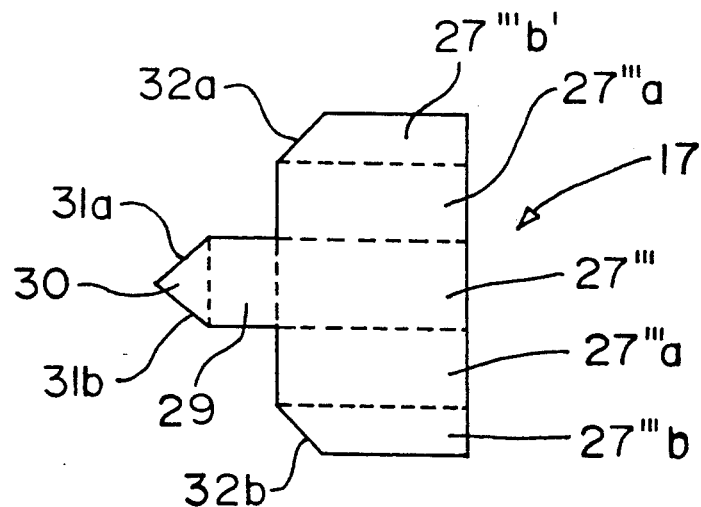

FIG. 10 illustrates another fibrous pad in an elevation plan view thereof prior to its folding, embodying the combined features of the pad 12 of FIG. 3 and pad 13 of FIG. 5, and which when mounted on a flat face of a distal end such as those of FIGS. 1 and 3 would have the elevation side appearance of the opposite side as shown in FIGS. 1 and 2 and the distal or terminal end appearances of FIGS. 4, 5, 7 and 8, with corresponding but different shapes as illustrated for FIG. 10.

DETAILED DESCRIPTION

The present inventions above-described in its various embodiments, is not meant to be a substitute for the typical conventional nylon toothbrush, for example. Instead, the device of the present invention is meant to be used as a supplement to a conventional tooth brush, more particularly the present invention's device being directed to the removal of stains, and/or plaque and/or tartar from the teeth of pets such as typically cats and/or dogs, i.e. to perform functions heretofore not readily nor adequately performed by the conventional nor prior art toothbrushes.

The inventive device as illustrated is typically a plastic handled device similar to that of a standard toothbrush. Instead of bristles, however, the cleaning device has a pad typically approximately about ⅜ inch wide and from about ¾ inch to about one and ¼th inch long by about ¼th inch high. Size is not critical except to the extent that larger sizes can be used for larger animals, while small sizes would be required for small pets, and except that normally reasonably smaller size (large enough to grasp and handle adequately) is more adept for use in getting into confined spaces and around various teeth and tooth surfaces. The pad is typically composed of fine preferably nylon or polyester fibers (but not necessarily limited thereto), and typically is impregnated with very fine and/or microscopic abrasive mineral particles as aforestated. Acrylic or phenolic resins hold the thin fibers together to form typically a pad and at the same time hold the tiny abrasive particles in place along each fiber or fibrous strand. A manufactured tradename of this abrasive pad material is SCOTCH-BRITE (trademark) having presently catalogue number 220 as manufactured by the 3M Company. Another typical product suitable for the present invention is the white fibrous scrubbing surface that is found on the sponge scrubber O-CEL-O (trademark) as manufactured by 3M Company, cat. 7215. The coated abrasive fiber pads may be of various degrees of abrasiveness. The typical pad is connected to the plastic handle by any conventional and/or suitable way and/or mechanism, but normally by using a cyanoacrylate glue or other satisfactory glue. In a two-sided embodiment, the second pad is composed of a plastic cellular sponge of approximately ⅛th inch thick, and a liquid applied typically acrylic abrasive coating and/or as is presently found in a product named SCROUNGE (trademark) that is manufactured by GUARDSMAN (trademark). This second pad is also attached to the plastic handle using a cyanoacrylate glue or any other satisfactory glue and/or conventional or other equivalent mechanism or composition.

It is not only not intended that the present device always necessarily be used alone devoid of complementing dentifrice, but the combination use of dentifrice with the abrasive scrubbing head-surface(s) of the present invention is most desirable for optimal and/or most effective cleaning. However, use of such dentifrice or the like, is not required nor essential nor critical to the beneficial use of the present inventive device. The second and additional abrasive surface and combination of the invention as illustrated on the opposite face, for FIGS. 1 through 3, is intended to be used and normally required—utilizing larger abrasive particles—to effectively clean-away plaque that is of the hardest variety; however, normally, the the embodiment embodying the microscopic sized abrasive mineral particles is more than adequate. A more preferred embodiment utilizes one or more of microscopic sized aluminum carbide resin and/or silicone carbinde resin as three-dimensional abrasive, and/or utilizes nylon fiber in the nowoven pad illustrated in the hereinafter described Figures.

Also, another manufacture of abrasive pads—of which the present invention is adapted to utilize the same type and/or identical pad material for the present inventive combination as above-described and claimed hereinafter, is the company Reckitt & Coleman, Inc. that produces "CHORE-BOY" (trademark) of which the white abrasive pad is mounted on a sponge, of which that pad is utilizable for the present invention.

A typical conventional glue suitable for use for gluing as previously noted, is cyanoacrylic glue known as "SUPER GLUE" (trademark), or any other satisfactory glue. A typical resilient material or sponge is plastic cellular sponge of commercially available conventional type. Liquid applied acrylic abrasive coating is conventionally commercially available, typically as for example found in a product above-noted, named "SCROUNGE" (trademark) manufactured by Guardsman Products, Inc.—apparently covered by U.S. Pat. No. 4,264,337.

While preferred abrasive composition non-toxic resins have been above specified as preferred embodiments of the invention, the invention clearly is not limited thereto, any non-toxic water-insoluble resin which in its original or conventionally modified states is suitable for anchoring and embodying typically mineral (or other) abrasive particles, is suitable and is contemplated as within the scope of the present invention. Also, the hardness of the resin also may beneficially contribute to the successful removal of tartar, plaque and/or stains from the teeth of pets. Accordingly, it is noteworthy to recognize that resins fall into four basic groups—as listed in *LANGE'S HANDBOOK OF CHEMISTRY*, Twelfth Edition [copyrighted 1979, . . . ] (and also in subsequent editions as further supplemented) found on pages 7-436 through 7-445, all within the contemplation and application as a part of the present invention, namely: a) natural gum resins of vegetable origin which contain some resinous constituents in admixture with carbohydrate bodies, so that the resulting complex will yield some water-soluble constituents; b) natural resins of animal origin; and c) new resin (same as natural gum resins, but with the solvents gone completely) and d) natural hydrocarbon resins. Typical of these resins are—gum accroides which typically heretofore have been used to color spirit varnishes and nitrocellulose liquors and in sealing wax, typically derived from a species of yellow or red Xanthorroea in Australia, and also Gum benzoin (composed of 69% cinnamic acid esters, 30% cinnamic acid and 1% or less of vanillin taken from Sumatra and Siam Styrax Benzoin, and Cameron Copal from West Africa, and Canadian Balsam—used in optometric work, from abies balsamea, and many others such as Columbia Copal, Congo Copal, Copaiba Baisam, Dammar, Demerara Copal, Dragon's Blood, East India, Gakbabynm Gamboge, Gilsonite, Gurjun Balsam, Jalap (resin of), Kaaraya gum (India Gum), etc., as typically set-forth in the Physical and Chemical Properties Natural Resin-list of Organic Chemistry handbook.

Natural resins are typically vegetable-derived and are typically amorphous mixtures of carboxylic acids, essential oils and terpenes occuring as exudations on the bark of many varieties of trees and/or shrubs. They are typically combustible, electrically nonconductive, hard and glassy with conchoidal fracture(s) when cold, and soft and sticky below the glass transformation point. Most are soluble in alcohol, ethers and carbon disulfide, and insoluble in water. The best known of these are rosin and balsam, obtained from coniferous trees; these have a high acid content. Of more remote origin are such resins as kauri, congo, dammar, mastic, sandarac, and copal. Their typical use is in varnishes, adhesives and printing inks, as well as in synthetic products. Miscellaneous types of natural resins include shellac, obtained from the secretion of an Indian insect, typically used as a transparent coating.; also there is amber which is a hard, polymerized resin that occurs as a fossil. Ester gum is a modified resin.

Acrylic fiber is a generic name for a manufactured fiber that is conventional and well known, in which the fiber-forming substance is any long-chain synthetic polymer composed of at least 85% by weight of acrylonitrile units (by definition of the Federal Trade Commission), having typically a tensile strength of 2 to 3 g/denier, and water absorption of 1.5 to 2.5% with typically a specific gravity of about 1.17. Acrylic resin is a composition of thermoplastic polymers and/or copolymers of acrylic acid, methacrylic acid, esters of these acids, or acrylonitrile. The monomers are colorless liquids that polymerize readily in the presence of light, heat, or catalyst such as benzoyl peroxide. Acrylic resins vary from hard, brittle solids to fibrous, elastomeric structures to viscous liquids, depending on the monomer used and the method of conventional polymerization. The production of acrylic fibers is conventional well known technology within the public domain.

As set forth in *Hackh's Chemical Dictionary*, Fourth Edition (and subsequent edition with supplemental description) at page 534, polyester is any polymer having structural units linked by ester groupings, obtained by conventional or other condensation of carboxylic acids with polyhydric alcohols. The polyester resin may be any of a group of synthetic resins which are polycondensation products of dicarboxylic acids with dihydroxy alcohols and are a special type of alkyd resin, but unlike other types, are not usually modified with fatty acids or drying oils. An outstanding characteric of these resins in their ability, when catalyzed, to cure or harden at room temperature under little or no pressure. Most polyesters now conventionally produced contain ethylenic unsaturation, generally introduced by unsaturated acids. The unsaturated polyesters are usually crosslinked through their double bonds with a compatible monomer, also containing ethylenic unsaturation, and thus becoming thermosetting. The principal unsaturated acids used are maleic and fumaric. Saturated acids, usually phthalic and adipic, may also be included. The function of these acids is to reduce the amount of unsaturation in the final resin, making it tougher and more flexible. The acid anydrides are often used if and when deemed desirable, and if conveniently available and/or applicable. The dihydroxy alcohols most generally used are ethylene, propylene, diethylene, and dipropylene glycols. Styrene and diallyphthalate are the most common cross-linking agents. Polyesters are resistant to corrosion, chemicals, solvents, etc, and are typically available as fibers, films, sheets, power and chips, for example. A polyester fiber is a generic name for a manufactured fiber (either as staple or continuous filament) in which the fiber-forming substance is any long chain synthetic polymer composed of at least 85% by weight of an ester of a dihydric alcohol and terephthalic acid (Federal Trade Commission). A typical one thereof is the Du Pont de Nemours Co. fiber designated DACRON (trademark) which is polyethylene terephthalate having typically a strength (staple) of 2.2 to 4.0 g. per denier, normally continuous filament having stength up to about 9.5 g per denier, with a melting point of about 264 degrees Centigrade, a water absorption of about 0.5%, and is nonflammable. Polyester resin is used in production of polyester fibers as conventional well known technology within the public domain. Typically and preferably the fibrous pad utilized for this invention, consistent with preceeding description(s), is nylon fiber, as a non-woven product characterized typically to be in the form of a porous pad or sponge in nature, herein referred to as a pad. As above described, the upper surface of the pad is more dense and/or tougher than cut-sides of the pad structure, and has found by the inventor to be less likely to dissentigrate and/or abrade-away, as contrasted to sides of the cut pad. Accordingly, by the pad being folded-under itself at the edged and/or at the end thereof, solely the tougher more durable upper surface upper face is exposed to abrading, now being also the side faces, as well as being the lower surface of the folded-under portion, the underturned surface being typically glued to the substantially flat face of the distal end of the handle member. However, the attachment may be by any appropriate and/or conventional means and/or mechanism desired and/or of a prior art nature, such as barbs extending from the substantially flat face of the distal end, and-or by some variety of staple or brad mechanism, or the like. However attaching by an adhesive has proven to be adequately satisfactory.

The foregoing turned-under structure, the convoluted convex outer side faces one or more thereof helps keep the pad surface away from the delicate tissue above the gums of the pet, while the pad is being abrasively rubbed horizontally across the teeth. Also the folded pad creates a double thickness of the pad—which has already been compacted while being folded and glued. The pad in the folded and compacted state now retains its shape after repeated uses. The folded pad accepts dentifrice and retains the dentifrice within the pad while the teeth are being scrubbed. The ends of the folded pad are reinforced by their double thickness and by the rolled edges of the sides of the pad. The squared edge of the end of the rolled pad can be used to get close to the gums to remove plaque and tarter. The end of the folded pad also keeps its shape after repeated use. The folded double thick pad is adheared to the handle very tightly due to the compactness and unity of the folded pad. The overall appearance of the pad is neat and compact and does not have layers of fiber ends exposed. The size of the tooth cleaning device may vary depending upon the size of the pet, to be potentially manufactured in different embodiments to have different sizes available. There may be various degrees of abrasiveness of the different available pads for alternate embodiments of the device(s), such that some are for conventional use, while others are for more stingent tarter-removing tasks beyond the normal. The most abrasive pad typically will be used to remove the built-up crystallized tartar, and the less abrasive pads typically will be used for removing merely plaques, typically for example. An anti-fungal additive may be applied during the manufacturing process of the fiber pad, to prevent fungus grownth while the scrubbing the teeth and/or between consecutive repeated uses thereof.

In the following detailed description of the above-described Figures, common indicia are utilized for the same elements of different figures of the same embodiment, and related indicia are utilized for different embodiment(s) of other figures for elements of corresponding shape and/or function, to improve ease of understanding and following the invention. Once an element has been described, description is not repeated for other figures nor embodiment(s).

Figure 6:
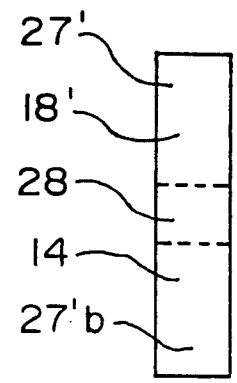
FIG. 6 illustrates the same fibrous pad of FIGS. 4 and 5, but in greater detail, in an elevation plan view thereof prior to its folding.
Figure 7:
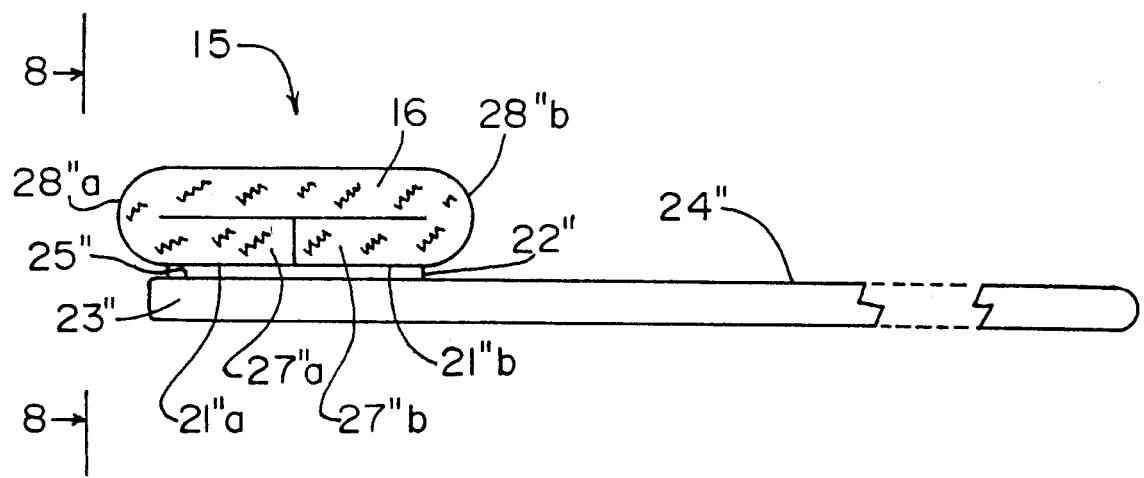
FIG. 7 illustrates an elevation plan side view of another alternate other embodiment of the invention shown in-part view of the handle portion.

FIG. 1 illustrates a cleaning device 11 of this invention illustrated in side view, FIG. 4 illustrating an alternate embodiment in side view, and FIG. 7 representing another alternate embodiment, with FIG. 10 illustrating a further pad combining the features of the pad 12 of FIGS. 1 through 3 and the pad 13 of FIGS. 4 through 6.

In FIG. 1, the device 11 includes the pad 12 mounted on the distal end 23 of the elongated structure having a handle end 24 for grasping with the fingers or hand in order to manipulate the device 11 when cleaning the teeth of a pet. The distal end 23 has a terminal-end upright face (side face) 23c and a lateral side face 23b illustrated and has an upper substantially flat face 25. The sponge-like pad 12 has an upper tough face (surface) 18 embodying the same abrasive as previously described for the entire pad. The exposed ends 19a and 19b of the mounted pad 12, being side-portions of the pad that are not turned under, each are the same as interior composition such as sponge-like fibrous composition 19 of FIG. 2 shown in that cross-sectional view, in which exposed ends 19a and 19b are less durable than the FIG. 2 convoluted convex side portions 20a and 20b of the turned-under pad. The FIG. 1 pad 11 has its upper face 18 (above-note) and underside 26 shown in the cross-sectional view of FIG. 2. The turned-under pad 12 of FIGS. 1 and 2 have the differently-located portions as symbolically identified in FIG. 3, as intermediate portion 27 and (when mounted) upright portions in the form of convoluted convex side portions 27a and 27a', and the turned-under pad portions 27b and 27b'. The turned-under pad portions have lower surfaces 21a and 21b respectively (of FIG. 2) broadly referred to as lower surface 21 of FIG. 1, each of which are glued by glue layer 22 to the substantially flat face 25. Also shown is the terminal end upright end above-noted side-face 23c and above-noted lateral side face 23b that are a part of the overal circumscribing side face made up of serially consecutive side faces 23a, 23b and 23c.

FIG. 2, apart from description thereof above, is a cross-sectional view as taken along line 2—2 of FIG. 1, through the pad of inner composition 19 and the distal end of the mounting-structure continuous with handle 24, the distal end having the mounting substantially flat face 25. In this FIG. 2, the convoluted convex shapes are discernible as curved side surface 20a of side portion 27a and convexly curved surface 20a' of side portion 27b. In this Figure, it can be seen that convoluted convex side portion and its curved side surface 20a extend outwardly beyond and overhang the head 23 side face 23a that is a part of the circumscribing side face inclusive of 23a, 23b and 23c.

FIG. 3 illustrates a plan view of the unfolded pad prior to folding-under, illustrates the typical shape and different portions thereof described-above for the embodiments of FIGS. 1 and 2.

FIG. 4 illustrates an alternate embodiment, in which the pad 14 is folded under at the terminal distal end of the mounting substantially flat face, such that the terminal end portion's surface 28 is of durable tough texture—being the same surface composition as FIG. 1 surface. The exposed non-hardened surface 29 is comparable to the FIG. 1 surfaces 19a and 19b. In this embodiment, typically the portion 27' layer is anchored to the lower turned-under portion 27'b by adhesive layer 22'a, and the lower surface 27'b is adhered to the flat upper face 25' by adhesive 22'. In this embodiment, it is seen that the convoluted convex portion's surface 28 extends beyond and thus overhangs the terminal end side-face 23'c that is a part of the circumscribing side face inclusive of 23'a, 23'b and 23'c.

FIG. 5 illustrates a distal end elevation plan view of the device 13, giving an elevation plan view of the convoluted convex end-portion 28, with the adhesive layer 22' adhering the pad to the substantially flat upper face 25'.

FIG. 6 illustrates the bent-under pad 14 of FIGS. 4 and 5, prior to bending under, illustrating symbolically the separate typical relative size(s) and shaped proportionate portions thereof, including of the top portion 27' and front convoluted convex portion surface (and portion thereof) 28 and bottom portion (27'b) to be turned-under.

FIG. 7 illustrates an embodiment basically similar to that of FIG. 5, except that also the opposite end of the elongated pad 16 is similarly turned-under to result in convoluted convex end portion surface (and portion thereof) 28"b and turned-under portion 27"b, portion 27"b being also adhered to the substantially flat mounting face 25". In this embodiment as was the situation in the embodiment of FIG. 4, it is seen that the convoluted convex portion's surface 28"a extends beyond and thus overhangs the terminal end side-face 23"c that is a part of the circumscribing side face inclusive of 23"a, 23"b and 23"c.

Figure 8:
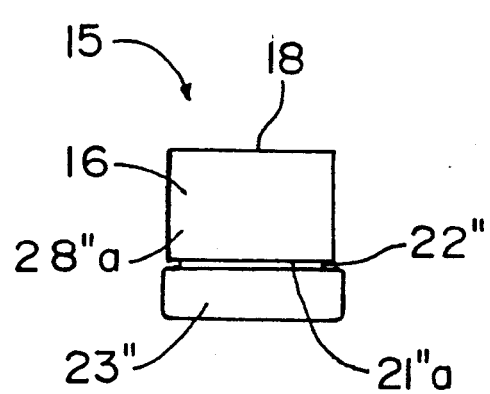
FIG. 8 illustrates and end elevation plan view of the embodiment of FIG. 7, as taken along lines 8—8 of FIG. 7.

FIG. 8 illustrates an end view of the embodiment of FIG. 7, as taken along line 8 thereof, all corresponding elements having been previously described.

Figure 9:
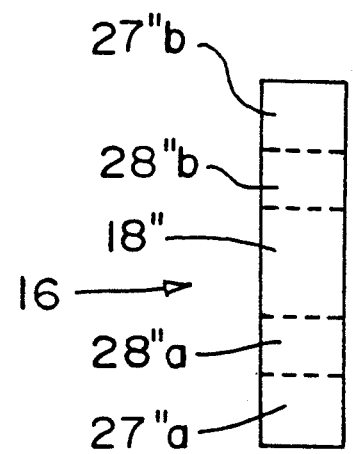
FIG. 9 illustrates the same fibrous pad of FIGS. 7 and 8, but in greater detail, in an elevation plan view thereof prior to its folding.

FIG. 9 illustrates a pad corresponding substantially in shape to that of FIG. 6, except having additionally the opposite turned under section, prior to the turning under thereof, as identified in FIG. 4.

FIG. 10 illustrates an additional embodiment which corresponds basically to the shape of the pad of FIG. 3, except having additionally the distal-end surface (and portion thereof) extension 29 and turnable-under portion 30, the portion 29 when turned downwardly forming the convoluted convex shape the same as the FIG. 7 embodiment's convoluted distal end pad surface 28'a. The angular edge 31a when folded under becomes flush with the angular edge 32a when folded under, and likewise edge 31b becomes flush with edge 32b when they are folded under. Otherwise, the separate portions thereof correspond in identity thereof substantially to those of the embodiment of FIG. 3.

It is within the scope and contemplation of the present invention to make such variations and modifications and substitution of equivalents and the like, as would be within the skill of an ordinary artisan in this field.

I claim:

1. A portable handle-mounted pet teeth-cleaning device comprising in combination: a teeth surface-cleaning means for rubbing against teeth surfaces to clean debris from surfaces of teeth of a pet; said teeth surface-cleaning means including a teeth-cleaning pad structure; a handle means for mounting thereof the teeth surface-cleaning means and for grasping thereof with fingers of a person cleaning a pet's teeth and for maneuvering the teeth surface-cleaning means against a pet's teeth during cleaning of debris from a pet's teeth, the handle means having an elongated distal end with a substantially flattened face adapted to mount permanently the teeth-cleaning pad structure thereagainst; pad mounting means securing said teeth-cleaning pad structure onto said substantially flattened face; said teeth-cleaning pad structure including a substantially flexible flattened elongated pad having opposite first and second end-portions and an intermediate portion therebetween and the flexible flattened elongated pad having opposite first and second faces extending between said opposite first and second end-portions, and there being a thickness between said first and second faces forming opposite side third and fourth faces respectively one thereof at each of said first and second opposite end-portions, each of said opposite side third and fourth faces having substantially said thickness, said opposite first face having a substantially durably hardened exterior face that is substantially resistent to significant abrasion when rubbing against a pet's tooth surfaces to remove debris from the tooth surfaces of a pet, at least one of said end portions being downwardly bent sufficiently to form at least one convoluted convex outer side face positioned above said flattened face and one turned-under portion positioned partially beneath said intermediate portion, said at least one turned-under portion having a lower-most face, each said lower-most face being permanently mounted by said pad mounting means onto said substantially flattened face of said elongated distal end, said elongated distal end having a circumscribing side face circumscribing said substantially flattened face, said at least one convoluted convex outer side face being positioned sufficiently laterally as to be positioned beyond said circumscribing side face a predetermined distance sufficient that said at least one convoluted convex outer side face may be abrasively rubbed against tooth surfaces devoid of contacting gum and tooth surfaces with said circumscribing side face.

2. The portable handle-mounted pet teeth-cleaning device of claim 1, in which said flattened face extends substantially longitudinally along a longitudinal axis of said elongated distal end, and in which each of said end-portions extends substantially transversely to said longitudinal axis of said elongated distal end, each of the end portions having a convoluted convex outer side face forming opposite first and second convoluted convex outer side faces and each of the end portions having a turned-under portion forming first and second turned-under portions substantially in juxtaposition to one another.

3. The portable handle-mounted pet teeth-cleaning device of claim 2, in which said opposite side faces each consists essentially of abrasive composition sufficiently abrasive to abrade away residual coating debris from tooth surfaces of a pet's teeth when rubbed thereagainst.

4. The portable handle-mounted pet teeth-cleaning device of claim 2, in which said first opposite face consists essentially of abrasive composition sufficiently abrasive to abrade away residual coating debris from tooth surfaces of a pet's teeth when rubbed thereagainst.

5. The portable handle-mounted pet teeth-cleaning device of claim 4, in which said abrasive composition comprises at least predominantly nontoxic resinous composition.

6. The portable handle-mounted pet teeth-cleaning device of claim 5, in which said resinous composition consists essentially of predominantly at least one of a phenolic resin and an acrylic resin.

7. The portable handle-mounted pet teeth-cleaning device of claim 5, in which said first abrasive composition includes first mineral particles supported by said resinous composition on a plurality of synthetic fibrous strands.

8. The portable handle-mounted pet teeth-cleaning device of claim 7, in which said mineral particles are microscopic in size.

9. The portable handle-mounted pet teeth-cleaning device of claim 7, in which said synthetic fibrous strands includes predominantly at least one of nylon strands and polyester strands.

10. The portable handle-mounted pet teeth-cleaning device of claim 4, in which said abrasive composition consists essentially of a plurality of strands of synthetic fiber coated by said nontoxic resinous composition.

11. The portable handle-mounted pet teeth-cleaning device of claim 1, in which said opposite side faces each consists essentially of abrasive composition sufficiently abrasive to abrade away residual coating debris from tooth surfaces of a pet's teeth when rubbed thereagainst.

12. The portable handle-mounted pet teeth-cleaning device of claim 1, in which said first opposite face consists essentially of abrasive composition sufficiently abrasive to abrade away residual coating debris from tooth surfaces of a pet's teeth when rubbed thereagainst.

13. The portable handle-mounted pet teeth-cleaning device of claim 12, in which said abrasive composition comprises at least predominantly nontoxic resinous composition.

14. The portable handle-mounted pet teeth-cleaning device of claim 13, in which said abrasive composition consists essentially of a plurality of strands of synthetic fiber coated by said nontoxic resinous composition.

15. The portable handle-mounted pet teeth-cleaning device of claim 14, in which said resinous composition consists essentially of predominantly at least one of a phenolic resin and an acrylic resin.

16. The portable handle-mounted pet teeth-cleaning device of claim 15, in which said abrasive composition includes first mineral particles supported by said resinous composition on at least said plurality of synthetic fibrous strands.

17. The portable handle-mounted pet teeth-cleaning device of claim 16, in which said mineral particles are microscopic in size.

18. The portable handle-mounted pet teeth-cleaning device of claim 17, in which said synthetic fibrous strands includes predominantly at least one of nylon strands and polyester strands.

19. The portable handle-mounted pet teeth-cleaning device of claim 1, in which said elongated distal end has a terminal distal portion, said flattened face extends substantially longitudinally along a longitudinal axis of said elongated distal end to said terminal portion, and in which said pad structure extends substantially longitudinally along said longitudinal axis of said elongated distal end, at least one of the end portions being turned-under, at said terminal distal end.

* * * * *